(12) United States Patent
Lygin et al.

(10) Patent No.: US 10,596,539 B2
(45) Date of Patent: Mar. 24, 2020

(54) METHOD FOR CARRYING OUT A HETEROGENEOUSLY CATALYSED REACTION

(71) Applicant: Evonik Roehm GmbH, Darmstadt (DE)

(72) Inventors: Alexander Lygin, Griesheim (DE); Matthias Groemping, Darmstadt (DE); Steffen Krill, Muehltal (DE)

(73) Assignee: Roehm GmbH, Darmstadt (DE)

( * ) Notice: Subject to any disclaimer, the term of this patent is extended or adjusted under 35 U.S.C. 154(b) by 0 days.

(21) Appl. No.: 16/095,065

(22) PCT Filed: Apr. 13, 2017

(86) PCT No.: PCT/EP2017/058903
§ 371 (c)(1),
(2) Date: Oct. 19, 2018

(87) PCT Pub. No.: WO2017/182381
PCT Pub. Date: Oct. 26, 2017

(65) Prior Publication Data
US 2019/0099731 A1    Apr. 4, 2019

(30) Foreign Application Priority Data

Apr. 22, 2016 (EP) ..................................... 16166606

(51) Int. Cl.
| | | |
|---|---|---|
| *C07C 67/00* | (2006.01) | |
| *B01J 8/00* | (2006.01) | |
| *B01J 8/22* | (2006.01) | |
| *C07C 67/39* | (2006.01) | |
| *B01J 8/18* | (2006.01) | |

(52) U.S. Cl.
CPC ............... *B01J 8/228* (2013.01); *B01J 8/006* (2013.01); *B01J 8/1872* (2013.01); *B01J 8/226* (2013.01); *C07C 67/39* (2013.01); *B01J 2208/0084* (2013.01); *B01J 2208/00752* (2013.01); *B01J 2208/00761* (2013.01); *B01J 2208/00867* (2013.01); *B01J 2219/00768* (2013.01); *B01J 2219/185* (2013.01); *B01J 2219/1943* (2013.01); *B01J 2219/1946* (2013.01)

(58) Field of Classification Search
CPC .......... C07C 67/39; B01J 8/228; B01J 8/1872
See application file for complete search history.

(56) References Cited

U.S. PATENT DOCUMENTS

| | | |
|---|---|---|
| 5,417,930 A | 5/1995 | McDonald, Jr. et al. |
| 5,723,041 A | 3/1998 | Devanathan et al. |
| 5,856,533 A | 1/1999 | Sweeney et al. |
| 5,962,537 A | 10/1999 | Leviness |
| 5,969,178 A | 10/1999 | Okamoto et al. |
| 6,270,734 B1 | 8/2001 | Leviness |
| 9,617,199 B2 | 4/2017 | Krill et al. |
| 9,890,105 B2 | 2/2018 | Krill et al. |
| 9,963,417 B2 | 5/2018 | Krill et al. |
| 2009/0134064 A1 | 5/2009 | Reynolds |
| 2010/0160460 A1 | 6/2010 | Soto et al. |

FOREIGN PATENT DOCUMENTS

| | | |
|---|---|---|
| CN | 101314120 B | 5/2010 |
| CN | 104418309 B | 8/2016 |
| EP | 0 781 595 A1 | 7/1997 |
| EP | 1 674 449 A1 | 6/2006 |
| WO | WO 98/50493 A1 | 11/1998 |
| WO | WO 2012/152600 A1 | 11/2012 |

OTHER PUBLICATIONS

U.S. Appl. No. 15/543,291, filed Jul. 13, 2017, US 2018-0001307 A1, Lygin, A. et al.
U.S. Appl. No. 15/776,837, filed May 17, 2018, Lygin, A. et al.
U.S. Appl. No. 15/760,030, filed Mar. 14, 2018, US 2018-0251419 A1, Groemping, M. et al.
U.S. Appl. No. 15/753,206, filed Feb. 16, 2018, US 2018-0251418 A1, Krill, S. et al.
International Search Report dated Jul. 4, 2017 in PCT/EP2017/058903 filed on Apr. 13, 2017.

*Primary Examiner* — Sikarl A Witherspoon
(74) *Attorney, Agent, or Firm* — Oblon, McClelland, Maier & Neustadt, L.L.P.

(57) ABSTRACT

A process for performing a heterogeneously catalysed reaction in a three-phase reactor, where there is at least one liquid phase, at least one gaseous phase and at least one solid phase in the reactor and the reactor has at least two zones, with the reaction mixture being conveyed downward in zone 1, the reaction mixture being conveyed upward in zone 2, zones 1 and 2 being separated from one another by a dividing wall, and in that the ratio between the average catalyst concentrations in zone 2 and in zone 1 is greater than 2.

16 Claims, 1 Drawing Sheet

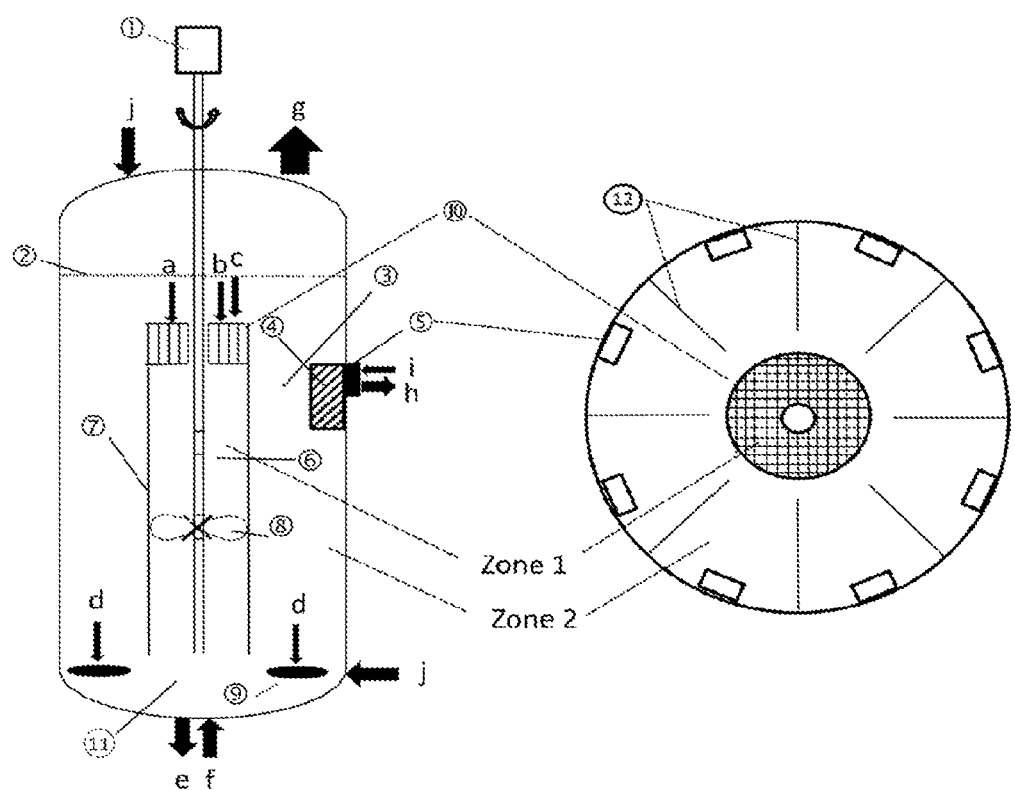

METHOD FOR CARRYING OUT A HETEROGENEOUSLY CATALYSED REACTION

FIELD OF THE INVENTION

The present invention relates to a novel process for performing a heterogeneously catalysed reaction, especially in a liquid phase.

There are plentiful descriptions in the technical literature of heterogeneously catalysed reactions in a liquid phase. These include, for example, the cobalt-catalysed Fischer-Tropsch synthesis, palladium- and nickel-catalysed hydrogenations with hydrogen, and numerous oxidation reactions.

Against this background, it has been possible by the present process according to the invention to perform such processes for longer periods without disruption, with constant or even increased activities and selectivities. This gives rise to the possibility of performing such processes in a very simple, economically viable and environmentally benign manner.

PRIOR ART

Heterogeneously catalysed processes in which at least one liquid phase is present are frequently performed in what are called slurry reactors. Slurry reactors are employed particularly for heterogeneously catalysed processes for which good mixing and low temperature and concentration gradients are advantageous. Particularly for strongly exothermic reactions, it is important to remove the heat of reaction as efficiently as possible. For this purpose, the reactors especially having internal or external circulation of the reaction mixture are of particularly good suitability.

A known variation of such reactors is that of reactors having an inner tube (draft tube), which enable internal circulation. For instance, U.S. Pat. No. 5,288,673 describes the use of a slurry reactor with a draft tube for a Fischer-Tropsch synthesis for preparation of hydrocarbons from synthesis gas.

CN 104418309 describes a slurry reactor with a draft tube for hydrogen peroxide production in a heterogeneously catalysed hydrogenation reaction of anthraquinone. The catalyst concentration used is about 10 g/l (<0.01 kg/kg of mixture) and is thus relatively low. The flow direction in the draft tube from the bottom upward constantly conveys a high proportion of the catalyst back into the tube.

WO 2012/152600 describes an ammoximation of cyclohexanone which is performed with a heterogeneous TS-1 catalyst as a three-phase reaction (gaseous-solid-liquid). Both the heat transfer and the mass transfer in this process can be distinctly improved when a cylindrical draft tube is used. The reactants are metered in here at different points. One metered addition is effected below the draft tube ($NH_3$ here), one from above it ($H_2O$ here) and optionally one from the side (cyclohexanone, for example, here). Filtration is effected with the aid of many candle filters having a high total area. These are positioned at the midpoint of the reactor height and at the outer edge of the draft tube. According to the description, the process can be performed without interruption and filter backwashing for 1 year. After one year, the filters then have to be cleaned.

There is no description of the use of slurry reactors with internal circulation for the reactions in which formation of deposits is possible, such as, more particularly, for reactions in which polymerizable substances, for example, are produced. U.S. Pat. No. 5,417,930 even suggests that a slurry-type reactor with internal circulation via one or more draft tubes can be particularly beneficial for the polymerization of polymerizable substances.

For reactions including such substances, there are therefore also some reactors in the prior art for the performance of a heterogeneously catalysed reaction with external circulation of the slurry mixture. For example, U.S. Pat. No. 5,969,178 describes a process for continuously preparing MMA from isobutene or tert-butanol via methacrolein. In this case, an oxidative esterification of readily polymerizable methacrolein takes place as the last step of the process in a bubble column with external circulation. In this respect, the reactor is described as an "external circulation type bubble column reactor".

CN 101314120 describes a loop slurry reactor with external circulation of the slurry mixture for performance of, for example, Fischer-Tropsch process.

All reactors having external circulation of the slurry mixture require quite complex reactor designs and slurry conveying apparatuses that have to be safeguarded, for example, by means of further pumps. Therefore, and for other reasons, these systems thus have disadvantages compared to systems having internal circulation.

In summary, the following aspects of the process according to the prior art are in need of improvement and desirable:
- very simple principle of reactor construction, combined with unlimited suitability for scale-up
- the use of substances that settle out or are readily polymerizable is possible
- use of high catalyst concentrations and hence higher throughput
- improved abrasion resistance of the heterogeneous catalyst used
- good mixing of the reactor phases
- long catalyst on-stream time, robust operation without interruption, very short maintenance phases if any
- the possibility of installation of simplified filtration systems for continuous separation of the heterogeneous catalyst from the slurry mixture without shutdown times

PROBLEM

In view of the prior art, the problem addressed by the present invention is therefore that of providing a technically improved process for performing a heterogeneously catalysed reaction, especially in a liquid phase. This novel process is especially to be afflicted with fewer disadvantages than conventional prior art processes.

More particularly, prior art processes are to be improved in such a way that there is only minimal catalyst abrasion, thus enabling a long on-stream time of the heterogeneous catalyst used with simultaneously good and virtually constant catalyst activity, selectivity and good mixing in the reactor.

Furthermore, the process, in the case of use of readily polymerizable reactants and formation of such products and/or by-products, is to enable such a reactor design that it permits only very minor polymerization at most.

Moreover, the process is to be inexpensive compared to the prior art, especially to be performable without any great catalyst losses as a result of abrasion or discharge, and is to implementable with fewer and shorter interruptions to operation.

Moreover, it should be possible to perform the process with relatively simple and inexpensive plants. The plants should accordingly be associated with low capital costs. At the same time, the plants should be simple to maintain, incur low maintenance costs and be operable safely.

Further objects not mentioned explicitly will become apparent from the overall context of the following description and the claims.

SOLUTION

These problems are solved by the provision of a novel process for performing a heterogeneously catalysed reaction in a three-phase reactor. This novel process is characterized in that at least one liquid phase, at least one gaseous phase and at least one solid phase are present in the reactor. The reactor has at least two zones. In zone 1, the reaction mixture is conveyed downward. In zone 2, the reaction mixture, in turn, is conveyed upward. Zones 1 and 2 are separated from one another by a dividing wall. During reactor operation, a significantly smaller amount of catalyst per unit volume generally remains suspended in zone 1 than in zone 2. Thus, the ratio between the average catalyst concentrations in zone 2 and in zone 1 is greater than 2, preferably greater than 5, especially greater than 10 and more preferably greater than 20. In very particularly preferred embodiments of the present invention, the ratio between the average catalyst concentrations in zone 1 and in zone 2 is actually greater than 100.

Zone 1 optimally has turbulent flow and hence very rapid mixing, while zone 2 has laminar flow at least in the upper portion, which is beneficial for optimal catalyst sedimentation.

Preference is given to an execution of the process according to the invention in which the gas required for the process, in the course of operation, is almost exclusively in zone 2, while zone 1 remains very substantially free of the undissolved gas.

A feature of a preferred execution of the present invention is the existence of a concentration gradient over the reactor height in zone 2: the greatest proportion of the complete catalyst mass is present in the lower portion of zone 2, while only a fraction thereof is in the upper portion of zone 2. This gives rise to a ratio between the catalyst concentration in zone 2 at 90% of the fill height of the reactor measured from the bottom to the catalyst concentration at 20% of the fill height measured from the bottom of less than 0.3. More preferably, this ratio is less than 0.2, even more preferably less than 0.1 and most preferably less than 0.05. While a catalyst concentration profile thus forms in accordance with the invention in zone 2, the catalyst concentration in zone 1 remains more or less constant at the level of the minimum catalyst concentration in the upper portion of zone 2. Thus, for example in an embodiment with a stirrer in zone 1, the stirrer comes into contact only with a fraction of the total amount of catalyst. This results in distinctly lower catalyst abrasion and an elevated catalyst on-stream time. Thus, the filters that are generally installed, which are used for the filtration of the product mixture, are also conserved and need little to no backwashing and/or no replacement.

These conditions can be realized in accordance with the invention, more particularly, through optimal performance of the reaction in a reactor according to the invention. As already described, such optimal performance may be characterized, for example, in that a catalyst concentration gradient forms over the reactor height in zone 2, with the maximum catalyst concentration close to the reactor base, while the minimum catalyst concentration is in the upper portion of the reactor. Such a catalyst concentration distribution can in turn be generated by means of an optimized flow profile within the reactor. For this purpose, the details given hereinafter can be applied.

Also preferred, or in addition to one or both of the aforementioned preferred embodiments of the invention, is a process in which the ratio between the average vertical flow rate in zone 1 and the average vertical flow rate in zone 2 is between 2 and 100, more preferably between 5 and 50 and especially preferably between 10 and 40.

In a particularly preferred embodiment of the present invention, the internal circulation between zones 1 and 2 in the reactor—irrespective of the other settings in the process—is assured by means of a draft tube (7). In this case, the flow of the reaction mixture in the draft tube (zone 1) is generated with the flow direction downward, whereas an opposite flow—from the bottom upward—is generated in the outside zone 2. This zone 2 is then the region between the draft tube and the reactor walls.

In such a "geodetic" mode of operation, the downward motion of the reaction mixture in zone 1 and the upward motion in zone 2 are optimized to one another.

Zone 1 is preferably a cylindrical draft tube, in which case the diameter of this draft tube can be varied over the reactor height. For example, it is preferable that the lower portion of the tube has a smaller diameter than the upper portion of this tube. Thus, a maximum flow rate in the downward direction and a significantly smaller flow rate in the upward direction is assured, which surprisingly distinctly minimizes the amount of the catalyst that gets back into the tube and has not been sedimented beforehand.

This can be explained in that such a distribution of zone 1 in the upper portion facilitates a fluid transition between the turbulent zone 1 and laminar zone 2, resulting in less entrainment of catalyst into zone 1.

This also has the surprising advantage that low catalyst abrasion occurs as a result, for example, of stirring or pumping in the tube. The preferred ratio between the diameter of the tube in the upper and lower portions of zone 1 is between 1 and 5, preferably between 2 and 4.

The reactor preferably has a cylindrical shape which is typical of pressure reactors, rounded off in the upper and lower portions. The optimal ratio between the reactor height and the reactor diameter is preferably between 1 and 3, more preferably between 1.1 and 2.5, most preferably between 1.3 and 2.3.

The diameter of the reactor can be varied over the reactor height. For example, it is preferable that the lower portion of the reactor has a smaller diameter than the upper portion of this reactor. Thus, it can be ensured that optimal mixing of the reaction mixture with the catalyst is generated in the lower portion of the reactor, while a very slow upward flow rate and good sedimentation of the catalyst is generated in the upper reactor portion. Thus, much less unsedimented catalyst can get back into zone 1 from zone 2, and hence much lower catalyst abrasion can result from the stirrer in zone 1.

Irrespective of the further performance of the process, a further adjustable feature of the invention is the ratio of the reactor diameter in the upper portion to that in the lower portion, which is preferably between 1 and 2, preferably between 1.1 and 1.5. More preferably, the ratio between the maximum and minimum reactor diameter is between 1 and 2, more preferably between 1.1 and 1.5.

For exact determination of the particular conditions, the wording "in the upper portion" should, for example, be determined such that a measurement is measured 10% of the total height below the uppermost end of the respective region. Analogously, the formulation "in the lower portion"

means that this range is correspondingly chosen at 10% above the lower end of the total height as the measurement point. An important factor for the more exact determination is that the distance from the upper end and from the lower end is identical in each case, and that this distance for the measurement is removed from the respective upper and lower ends of the apparatus by a maximum length corresponding to 20% of the total height of the apparatus to be measured (for example zone 1 or the overall reactor).

It has been found that, surprisingly, such a reactor form having a draft tube and internal circulation as described above does not only enable seamless operation, high catalyst effectiveness, good mixing and good heat removal, but also conserves the heterogeneous catalyst used in such a reactor in such a way that catalyst abrasion can be minimized and the catalyst on-stream time overall is increased. As a result, it is additionally also possible for the filters used to be operated without disruption for a longer period without any need for costly and inconvenient cleaning and/or filter replacement.

Thus, it is particularly advantageous to configure the process in such a way that optimal mixing of the reaction mixture with the catalyst is generated in the lower portion of the reactor, while a very slow upward flow rate and good sedimentation of the catalyst is brought about in the upper reactor portion. Thus, much less unsedimented catalyst can get into zone 1 from zone 2, and hence much lower catalyst abrasion can take place as a result of the stirrer in zone 1.

Further surprising advantages of the present process over the prior art include the fact that heat and mass transfer are good and, as a result, only very small temperature and concentration gradients arise, which is very beneficial for high activity and selectivity of the catalyst.

Furthermore, an optimal gas distribution for the three-phase reaction is present in the reactor. In addition, very robust performance of a heterogeneously catalysed reaction with high catalyst concentrations is possible by virtue of the process according to the invention.

Especially surprising, it has been found that the specific reactor construction, for example particular ratios of the reactor dimensions, the installation of a draft tube for catalyst protection, and position and construction of the sedimentation and filter system, play a major role for stable and efficient operation with relatively high catalyst concentrations without significant catalyst abrasion.

Irrespective of the other embodiments of the invention chosen, the reaction mixture is conveyed downward in zone 1, preferably by means of at least one pump or at least one stirrer. All stirrers that promote axial flow in the downward direction would be particularly appropriate for this purpose. Preferably, at least one propeller stirrer is used, more preferably at least two. In the case of one stirrer, it is preferably positioned in about the middle of the draft tube, whereas two stirrers are preferably installed in the middle and at the lower edge of the draft tube.

In addition, irrespective of the other embodiments of the invention chosen, preference is given to introducing at least one liquid feed stream into the upper portion of zone 1. More preferably, all liquid feed streams are introduced into the upper portion of zone 1.

Since the reactor is preferably to be used for a continuous process, the heterogeneous catalyst should preferably be continuously filtered out of the reaction mixture. For this purpose, preference is given to using filters present in the reactor, more preferably at the periphery in the upper portion of zone 2 of the reactor. More particularly, irrespective of the other embodiments of the invention chosen, preference is given to installing at least one continuously operable and backwashable filter in the upper portion of zone 2.

Alternatively or additionally, and as it were preferably, the reaction mixture is discharged continuously from the reactor and filtered through at least one external filter. Thereafter, the catalyst is optionally subjected to further treatment after the filtration and passed partly or completely back into the reactor. This further treatment may, for example, involve washing, reactivating or separation by particle size.

Upstream of such filters, it is preferably possible to install an additional sedimentation system, for example at the periphery of the reactor as well. This may be a specific zone with laminar flow, where a majority of the catalyst used is sedimented. Such sedimentation is thus effected before the actual filtration.

One possible variant of such a sedimentation system is, for example, an assembly composed of inclined elements, for example tubes, or inclined metal sheets (for example an inclined clarifier). The principle of function of such systems is further described in Journal of Fluid Mechanics/Volume 92/Issue 03/June 1979, pp 435-457 and "Enhanced sedimentation in vessels having inclined walls" in Theory of Dispersed Multiphase Flow: Proceedings of an Advanced Seminar Conducted by the Mathematics Research Center The University of Wisconsin-Madison May 26-28, 1982. Details of use for an oxidation reaction, for example, are given in JP 10-094705 A and JP 09-248403 A.

More preferably, the sedimentation system and filter are in the upper portion of the reactor, at such a position in zone 2 that the flow rate is at its slowest. This means, in turn, that the cross section of zone 2 has a maximum area at this point.

The filter porosity used with preference is between 5 and 100 micrometres, more preferably between 10 and 50 micrometres.

For additional retention of the fine catalyst particles, the reaction mixture, once it has been filtered through reactor filters (5), is preferably filtered at least once more through finer filters having porosity of 1 to 10 μm outside the reactor, such that the particles of not more than 5 μm are retained by the filter to an extent of at least 90%.

In an illustrative and particularly preferred embodiment according to FIG. 1, the reaction mixture, after the sedimentation system (4), passes through a plurality of filters (5) distributed homogeneously around the reactor and arrives at the further production workup steps. The filter and sedimentation system is preferably regularly backwashed, in order that a maximum amount of the heterogeneous catalyst remains catalytically active in the reactor and there is no blockage of the sedimentation system and the filters.

Irrespective of any filtration, there may preferably be one or more baffles (10), called swirl breakers, in the upper portion of zone 1. These counteract the effect of a vortex or funnel, in that the swirling of the liquid is broken and a gentle transition between the region outside and within zone 1 or the draft tube is enabled. More preferably, zone 2 is equipped with at least 2, more preferably with at least 4 and most preferably with at least 8 baffles and/or dividing walls. Thus, the radial flow rate in zone 2 can be drastically reduced and the sedimentation in the upper portion of zone 2 can be configured in a particularly effective manner.

Preferably, the gas required for the reaction is metered in in the finely dispersed state via the gas distributors (9), called spargers, in the lower reactor portion. Preferably, the gas used is metered in in the direction toward the reactor base, in order that a minimum level of blockage with the catalyst particles can occur.

In the case of a hydrogenation reaction, it is appropriate to use hydrogen or hydrogen-containing gas. In the case of an oxidation reaction, oxygen is utilized in the form of air or another $O_2$-containing mixture. In the case of Fischer-Tropsch synthesis, synthesis gas can serve as the gas. It is also possible to use other unspecified gases according to the desired reaction.

A liquid phase application appropriate for the reactor described is, for example, the hydrogenation of anthraquinone, which is used for hydrogen peroxide production. It is thus also possible to conduct fat hardening, i.e. hydrogenation of unsaturated fatty acids. Numerous other hydrogenations, for example of substances having multiple bonds, such as aromatics, alkenes or alkynes, nitro compounds, carbonyl compounds, etc. can also be conducted with the reactor type.

More preferably, the process according to the invention is applicable in the case of a heterogeneously catalysed oxidation reaction with an oxygen-containing gas. The oxygen concentration (partial $O_2$ pressure) in zone 2 has a gradient with a maximum $O_2$ concentration in the lower portion of zone 2 and a minimum $O_2$ concentration in the upper portion of this zone. More preferably, in such a process, the ratio between the oxygen concentration in the gas phase of zone 2 at 20% of the fill height of the reactor measured from the bottom and the oxygen concentration in the gas phase of zone 2 at 90% of the fill height measured from the bottom is greater than 2, preferably greater than 4.

Some examples of the appropriate oxidation processes in the liquid phase are, for example, specific oxidations of alkenes, alkylaromatics, oxidative esterification of aldehydes to carboxylic esters, for example the conversion of (meth)acrolein to alkyl (meth)acrylate, and further selective oxidation reactions in the specialties sector.

Most preferably, the heterogeneously catalysed reaction is a continuous oxidative esterification of methacrolein with oxygen and methanol for preparation of methyl methacrylate.

The heterogeneous catalysts used are preferably noble metal-containing, especially Pt-, Pd-, Ru-, Rh-, Ru-, Au- and/or Ag-containing, supported catalysts. The supports used may especially be mineral oxides, oxide mixtures, activated carbon, polymer materials or other substances. In addition, a catalyst used with preference for such an oxidation reaction has a mean diameter between 10 and 200 µm.

The catalyst used can be withdrawn from the reactor continuously or batchwise, for example for a washing and/or regenerating operation, for continuous monitoring/analysis or renewal. The connection point for catalyst withdrawal or supply is preferably in the lower portion of the reactor, where the catalyst concentration is at its highest. An alternatively preferred variant implies a catalyst withdrawal point in the upper portion of the reactor. In this case, preference is given to a point where the smallest catalyst particles in particular are present.

Apart from the reactants required for the reaction, various auxiliaries can be supplied to the process, for example acids, bases, polymerization inhibitors, antifoams, etc.

All high-reactivity (for example readily polymerizable) reactants and/or auxiliaries, for example a strong base, such as NaOH or KOH, or a strong acid, such as $H_2SO_4$ or HCl, should preferably be metered into the upper portion of zone 1. This ensures that these substances are mixed very rapidly with the reaction mixture before they can come into contact with the catalyst and the other reactants. This avoids local overheating and improves the selectivity and overall effectiveness of the target reaction.

DRAWINGS

List of reference numerals for FIG. 1

FIG. 1 is a specific configuration of a reactor usable in the process according to the invention. This constitutes an embodiment of the invention which is particularly suitable for oxidation reactions in particular. On the other hand, however, the drawing does not serve to restrict the scope of protection of the present application in any way. This drawing is simplified such that narrowings of the reactor or of zone 1, for example, are not depicted.

| | |
|---|---|
| 1: Motor | a: Feed 1 (reactant 1) |
| 2: Reaction mixture level | b: (optional) Feed 2 (reactant 2) |
| 3: Sedimentation zone (zone 2) | c: (optional) Feed 3 (auxiliary 1) |
| 4: (optional) Sedimentation system | d: Gas |
| 5: Filter system (with backwashing) | e: Catalyst slurry outlet |
| 6: Mixing/saturation zone (zone 1) | f: Catalyst slurry inlet |
| 7: Draft tube | g: Offgas outlet (to the condenser) |
| 8: at least one propeller stirrer | h: Product mixture outlet |
| 9: Air distribution nozzles (spargers) | i: Filter backwash |
| 10: Baffles (swirl breakers) | j: (optional) Inert gas purge |
| 11: Reaction zone (zone 2, lower portion) | |
| 12: Segment sheet components (baffles, dividing walls) | |

EXAMPLES

Example 1

The reactor (according to FIGURE) had the following ratios of the dimensions:

Reactor height/reactor diameter=1.6

Fill height with reaction mixture/reactor height=0.75

Reactor diameter (D2)/draft tube diameter (D1)=5.3

The ratio between the average vertical flow rates (in the downward direction) V1 in the draft tube (zone 1) and the the average vertical flow rates (in the upward direction) V2 in the zone 2 is: $V1/V2=(D2/D1)^2-1=27.4$ Performance of an Oxidative Esterification Reaction of Methacrolein to Methyl Methacrylate The pH of a 42.5% by weight solution of methacrolein (MAL) in methanol was adjusted to pH=7 with stirring by the addition of a 1% by weight solution of NaOH in methanol. This solution was fed at a constant feed rate continuously into the upper portion of the draft tube (zone 1) of the reactor usable in accordance with the invention according to FIG. 1 at pressure 5 bara and internal temperature 80° C. At the same time, a sufficient amount of 1% by weight NaOH solution in methanol, together with 600 g of Au/NiO/$SiO_2$—$Al_2O_3$—MgO powder catalyst (prepared according to Example 1 from the application EP 2 210 664 A1), was fed into this reactor (including in the upper portion of the draft tube) that the value pH=7 in the reactor remained constant. In the lower portion of the reactor, in zone 2, air was metered in via multiple gas distributors. The product mixture was separated from the majority of the heterogeneous catalyst by means of a continuously backwashable sedimentation system (inclined clarifier) present at the periphery of the upper portion of zone 2 and filtered through a filtration system and analysed by means of gas chromatography (GC).

After operation for 1 h, 3 samples of the product mixture were respectively taken at 20%, 50% and 90% of the fill height of the draft tube (zone 1), and three samples at 20%, 50% and 90% of the fill height of zone 2. The positions of the measurement points are always reported from the bottom. The solids content [in g/l] of the samples was determined.

The C90%/C20% ratio in zone 2 was less than 0.1.

The average concentration in zone 1 <C1> was calculated as the mean of the three samples from the draft tube:

$<C1> = (C1(20\%) + C1(50\%) + C1(90\%))/3$, with
$C1(20\%) \sim C1(50\%) \sim C1(90\%)$;

the average concentration in zone 2 <C2> was calculated as follows:

$<C1> = (\text{total mass of catalyst} - <C1>*V1)/V2$

<C2>/<C1> was greater than 10.

It was determined visually that air introduced via air distributors in the lower portion of zone 2, in the course of operation, was observed almost exclusively in zone 2, whereas zone 1 remained free at least of the gas undissolved in the reaction mixture.

Oxygen concentration in the gas phase of zone 2 at 20% of the fill height of the reactor measured from the bottom was $C(O_2)20\% \sim 21$ vol % $O_2$; oxygen concentration in the gas phase of zone 2 at 90% of the fill height measured from the bottom was $C(O_2)90\% \sim 5$ vol % $O_2$, and thus $C(O_2)20\%/C(O_2)90\% = 4.2$.

Thus, continuous undisrupted operation of the plant for several months was ensured.

Comparative Example 1

The reactor was identical to that used in Example 1, except for the draft tube which was absent. The reaction regime was identical to that in Example 1.

After 1 h, two samples of catalyst suspension were taken, respectively at sites at 20% and 90% of the fill height measured from the bottom. A solids content [in g/l] was determined therein. The ratio C90%/C20% was 0.31. <C1>=<C2>

Comparative Example 2

As Example 1, except that feed solutions were not introduced into the draft tube but into zone 2.

The particle size distribution (measured by the laser diffraction method) of the fresh catalyst, and of the catalyst after the test in Example 1 (after 1000 h) and after the test in Comparative Examples 1 and 2 (after 1000 h in each case) is summarized in the table below. Activity and selectivity of the catalyst after 200 h and 1000 h in each case is likewise reported for all examples:

|  | $D_{50}$ [μm] | STY [mol MMA/kg-h] | S (MMA) [%] |
|---|---|---|---|
| Fresh catalyst | 61.5 | | |
| E1 (200 h) | | 8.5 | 95.7 |
| E1 (1000 h) | 60.4 | 8.5 | 95.6 |
| CE1 (200 h) | | 8.5 | 95.7 |
| CE1 (1000 h) | 51.2 | 8.0 | 93.3 |
| CE2 (200 h) | | 8.2 | 92.4 |
| CE2 (1000 h) | 60.3 | 8.0 | 90.1 |

It was observed that the mechanical abrasion of the catalyst in a reactor according to the invention having a draft tube (Example 1; E1) was lower than the abrasion in the reactor without a draft tube (Comparative Example 1; CE1). It was also observed that the activity and selectivity of the catalyst used decreased after an operating time of 1000 hours.

In the embodiment with the addition of feed into zone 2 (Comparative Example 2; CE2), selectivity for MMA was much smaller again.

Example 2

Similar to Example 1, but with no internal filter in the reactor after the sedimentation system. The reaction mixture was alternately filtered through one of two external filters installed in parallel with porosity 10 micrometres, with one filter constantly in use and the other simultaneously being backwashed. The catalyst remaining on the filter was returned to the reactor. Thus, continuous undisrupted operation of the plant for several months was ensured.

Comparative Example 3

As Example 2, except using no sedimentation system (no inclined clarifier). Much more catalyst arrived continuously at the external filter. The filter switching cycle (switching to backwashing mode) had to be distinctly shortened in order that it was possible to discharge a continuous reaction mixture output. After operation for 2 months, operation had to be stopped and the two filters used had to be washed intensively with NaOH solution before operation could continue.

It was observed that an internal sedimentation system, through prior removal of the majority of the solids, distinctly reduces the burden on the filters used and hence promotes undisrupted operation.

The invention claimed is:

1. A process for performing a heterogeneously catalysed reaction in a three-phase reactor having at least one liquid phase, at least one gaseous phase and at least one solid phase, the process comprising:
    conveying a reaction mixture downward in a first zone of the reactor; and then
    conveying the reaction mixture upward in a second zone of the reactor,
    wherein the first and second zones are separated from one another by a dividing wall,
    the first zone is substantially free of undissolved gas, and
    a ratio of an average catalyst concentration in the second zone to an average catalyst concentration in the first zone is greater than 2.

2. The process according to claim 1, wherein the ratio of the average catalyst concentrations in the second to first zone is greater than 5.

3. The process according to claim 1, wherein the gas required for the process, in the course of operation, is metered in in the finely dispersed state from a lower portion of the reactor.

4. The process according to claim 1, wherein a ratio of a catalyst concentration in the second zone at 90% of a fill height of the reactor measured from a bottom of the reactor to a catalyst concentration at 20% of the fill height measured from the bottom is less than 0.3.

5. The process according to claim 1, wherein a ratio of an average vertical flow rate in the first zone to an average vertical flow rate in the second zone is between 5 and 50.

6. The process according to claim 1, wherein a ratio of a reactor diameter in an upper portion to a reactor diameter in a lower portion is between 1 and 2.

7. The process according to claim 1, wherein a ratio of a diameter in an upper portion of the first zone to a diameter in a lower portion of the first zone is between 1 and 5.

8. The process according to claim 1, wherein the reaction mixture is conveyed downward in the first zone by at least one pump or at least one stirrer.

9. The process according to claim 1, wherein at least one liquid feed stream is introduced into an upper portion of the first zone.

10. The process according to claim 1, wherein at least one continuously operable and back-washable filter is installed in an upper portion of the second zone.

11. The process according to claim 1, wherein the reaction mixture is discharged continuously from the reactor and filtered through at least one external filter and the catalyst is passed back into the reactor after the filtration.

12. The process according to claim 1, wherein the second zone is divided into at least two segments by dividing walls, and at least one gas is metered in and finely distributed in a lower portion of the second zone.

13. The process according to claim 1, wherein the heterogeneously catalysed reaction is an oxidation reaction with an oxygen-containing gas.

14. The process according to claim 1, wherein a ratio of an oxygen concentration in the gas phase of the second zone at 20% of a fill height of the reactor measured from a bottom of the reactor to an oxygen concentration in the gas phase of the second zone at 90% of the fill height measured from the bottom is greater than 2.

15. The process according to claim 1, wherein the heterogeneously catalysed reaction is a continuous oxidative esterification of methacrolein with oxygen and methanol for preparation of methyl methacrylate.

16. A process for performing a continuous oxidative esterification of methacrolein with oxygen and methanol for preparation of methyl methacrylate in a three-phase reactor having at least one liquid phase, at least one gaseous phase and at least one solid phase, the process comprising:
conveying a reaction mixture downward in a first zone of the reactor; and
conveying the reaction mixture upward in a second zone of the reactor,
wherein the first and second zones are separated from one another by a dividing wall, and
a ratio of an average catalyst concentration in the second zone to an average catalyst concentration in the first zone is greater than 2.

* * * * *